United States Patent [19]

Straub et al.

[11] Patent Number: 5,478,937
[45] Date of Patent: Dec. 26, 1995

[54] CERTAIN CINNOLINE CARBOXALDEHYDES AND NAPHTHYRIDINE CARBOXALDEHYDES USEFUL AS INTERMEDIATES

[75] Inventors: Alexander Straub; Siegfried Goldmann, both of Wuppertal; Jürgen Stoltefuss, Haan; Martin Bechem, Wuppertal; Ranier Gross, Wuppertal; Siegbert Hebisch, Wuppertal; Joachim Hütter, Wuppertal; Howard-Paul Rounding, Wuppertal, all of Germany

[73] Assignee: Bayer Aktiengesellschaft, Leverkusen, Germany

[21] Appl. No.: 377,063

[22] Filed: Jan. 23, 1995

Related U.S. Application Data

[62] Division of Ser. No. 230,468, Apr. 20, 1994, Pat. No. 5,434,153.

[30] Foreign Application Priority Data

Apr. 27, 1993 [DE] Germany ............ 43 136 96.6

[51] Int. Cl.$^6$ .................. C07D 237/28; C07D 471/04
[52] U.S. Cl. ............. 544/235; 546/122; 546/123
[58] Field of Search .................. 546/122, 123; 544/235

[56] References Cited

U.S. PATENT DOCUMENTS

| | | | |
|---|---|---|---|
| 3,862,162 | 1/1975 | Meyer et al. | 546/310 |
| 3,946,026 | 3/1976 | Meyer et al. | 546/309 |
| 3,989,708 | 11/1976 | Meyer et al. | 546/310 |
| 4,555,512 | 11/1985 | Goldmann et al. | 514/302 |
| 5,200,420 | 4/1993 | Goldmann et al. | 514/338 |
| 5,225,558 | 7/1993 | Stoltefuss et al. | 546/167 |
| 5,254,692 | 10/1993 | Goldmann et al. | 548/152 |
| 5,410,055 | 4/1995 | Straub et al. | 544/235 |

FOREIGN PATENT DOCUMENTS

| | | |
|---|---|---|
| 2639257 | 3/1978 | European Pat. Off. . |
| 0515940 | 12/1992 | European Pat. Off. . |
| 0538690 | 4/1993 | European Pat. Off. . |

OTHER PUBLICATIONS

Straub, Synthetic Comm., 23 (3), pp. 365–372, Mar. 1993.
Chemical Abstracts, vol. 88, No. 17, Apr. 17, 1978, CA#120947c.
Chemical Abstracts, vol. 118, No. 23, Jun. 7, 1993 CA#233917z.
Chemical Abstracts, vol. 108, No. 13, Mar. 28, 1988, CA#112361y.
Chemical Abstracts, vol. 100, No. 11, Mar. 12, 1984, CA#85564t.

*Primary Examiner*—Bernard Dentz
*Attorney, Agent, or Firm*—Sprung Horn Kramer & Woods

[57] ABSTRACT

The present invention relates to new 2-amino-4-heteroaryl-1,4-dihydropyridines of the general formula (I)

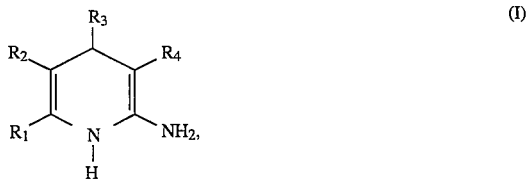

(I)

in which $R_1$ to $R_4$ have the meaning given in the description, processes for their preparation and their use in medicaments, in particular in compositions for the treatment of cardiovascular disorders.

1 Claim, No Drawings

CERTAIN CINNOLINE CARBOXALDEHYDES AND NAPHTHYRIDINE CARBOXALDEHYDES USEFUL AS INTERMEDIATES

This is a division of U.S. application Ser. No. 08/230,468, filed on Apr. 20, 1994, now U.S. Pat. No. 5,434,153.

The present invention relates to novel 2-amino-4-heteroaryl- 1,4-dihydropyridines, processes for their preparation and their use in medicaments, in particular in compositions for the treatment of cardiovascular disorders.

It is already known that, in addition to an anti-arrhythmic action, some 2- and 6-amino-3,4-dihydropyridines also have a lipid absorption-inhibiting action.

In addition, 2-amino-1,4-dihydropyridines having a vasodilatory and anti-hypertensive action have also been described and others with a positively inotropic action and largely neutral behaviour to the vascular system have been disclosed [cf. EP 515,940]. 1,4-Dihydropyridines with positively inotropic action, which are substituted in the 4-position by heterocycles, are likewise known [cf. EP A 450,420].

Certain 4-thiochromonyl-substituted 1,4-dihydropyridines are embraced by the general description of EP A 123,095 without actual substance representatives being mentioned there.

The present invention relates to new 2-amino-4-heteroaryl- 1,4-dihydropyridines of the general formula (I)

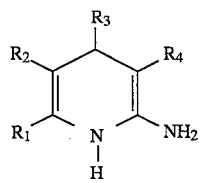

in which

R$^1$ represents straight-chain or branched alkyl having up to 8 carbon atoms, which is optionally substituted by hydroxyl, R$^2$ represents straight-chain or branched alkoxycarbonyl, having up to 6 carbon atoms, which is optionally substituted by straight-chain or branched alkoxy having up to 4 carbon atoms, represents nitro, cyano or formyl, or R$^1$ and R$^2$ together form a ring of the formula

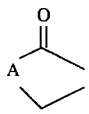

in which

A denotes an oxygen or sulphur atom, the —CH$_2$— or —CH$_2$CH$_2$— group,

R$^3$ represents a heterocyclic aryl radical of the formula

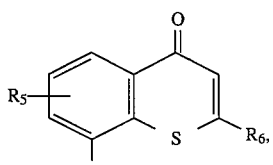

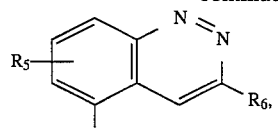

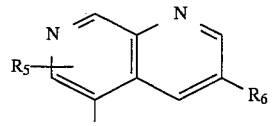

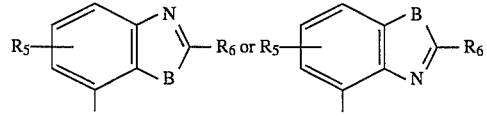

in which

B denotes an oxygen or sulphur atom,

R$^5$ denotes hydrogen, halogen or straight-chain or branched alkyl or alkoxy in each case having up to 8 carbon atoms, R$^6$ denotes aryl having 6 to 10 carbon atoms, which is optionally substituted up to 2 times by identical or different substituents from the group consisting of halogen, nitro, cyano, trifluoromethyl, trifluoromethoxy, trifluoromethylthio, straight-chain or branched alkyl, alkoxy or alkoxycarbonyl in each case having up to 8 carbon atoms and carboxyl, or denotes straight-chain or branched alkyl having up to 12 carbon atoms, or denotes cycloalkyl having 3 to 8 carbon atoms, or denotes pyridyl or thienyl, which is optionally substituted by halogen, R$^4$ represents a group of the formula —CO—NR$^7$R$^8$, —CO—D—R$^9$ or —P(O)(OR$^{10}$)(OR$^{11}$), in which R$^7$ and R$^8$ are identical or different and denote hydrogen or a straight-chain, branched, cyclic, saturated or unsaturated hydrocarbon radical having up to 10 carbon atoms, which is optionally substituted by cycloalkyl having 3 to 8 carbon atoms, halogen, hydroxyl, cyano or by aryl, aryloxy or arylthio in each case having 6 to 10 carbon atoms or by a 5- to 7-membered, saturated or unsaturated heterocycle having up to 3 heteroatoms from the group consisting of S, N and O, where the cycles for their part can be substituted by halogen, cyano or by straight-chain or branched alkyl, alkoxy, alkylthio, alkoxycarbonyl, halogenoalkyl, halogenoalkoxy or halogenoalkylthio in each case having up to 4 carbon atoms, or denote aryl having 6 to 10 carbon atoms or a 5- to 7-membered, saturated or unsaturated heterocycle having up to 3 heteroatoms from the group consisting of S, N and O and which are optionally substituted up to 2 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or R$^7$ and R$^8$ together, including the nitrogen atom, form a 5- to 8-membered, saturated or unsaturated heterocycle which is optionally interrupted by an oxygen atom or by a radical of the formula S(O)$_a$, —CO— or —NR$^{12}$, in which a denotes a number 0, 1 or 2, $R^{12}$ denotes hydrogen or aryl having 6 to 10 carbon atoms, which is optionally substituted up to 2 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or denotes a cyclic, straight-chain or branched, saturated or unsaturated hydrocarbon radical having up to 8 carbon atoms, which is optionally substituted by hydroxyl or halogen or by aryl having 6 to 10 carbon atoms or a 5- to 7-membered, saturated or unsaturated heterocycle having 3 heteroatoms from the group consisting of S, N and O, which for their part can be substituted up to 2 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, and the heterocycle is optionally substituted by straight-chain or branched alkoxy, or alkylthio in each case having up to 4 carbon atoms, halogen, aryl having 6 to 10 carbon atoms, a 4- to 7-membered, saturated or unsaturated heterocycle having up to 3 heteroatoms from the group consisting of S, N and O or by straight-chain or branched alkyl having up to 4 carbon atoms, which for its part can optionally be substituted by aryl having 6 to 10 carbon atoms, D denotes a direct bond or an oxygen atom, $R^9$ denotes hydrogen or aryl having 6 to 10 carbon atoms or a 4- to 7-membered, saturated or unsaturated heterocycle having up to 3 heteroatoms from the group consisting of S, N and O and which are optionally substituted up to 3 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or denotes a cyclic, straight-chain or branched, saturated or unsaturated hydrocarbon having up to 12 carbon atoms, which is optionally interrupted up to 3 times by identical or different oxygen or —CO—, —CO—NH—, —O—CO—, —CO—O—, —NH—CO—, —SO$_2$—NH—, —NH—SO$_2$—, —S(O)$_b$— or —NR$^{13}$, in which b has the abovementioned meaning of a and is identical to or different from this, $R^{13}$ has the abovementioned meaning of $R^{12}$ and is identical to or different from this, or the hydrocarbon radical is optionally interrupted up to 3 times by identical or different arylidene having 6 to 10 carbon atoms or a cyclic radical of the formula

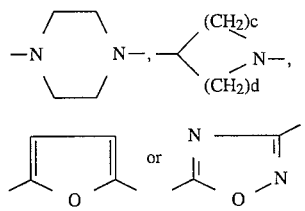

in which c and d are identical or different and denote a number 1 or 2, and in which arylidene and the cycles for their part can be substituted by halogen, cyano or by straight-chain or branched alkyl, alkoxy, alkylthio, alkoxycarbonyl, halogenoalkyl, halogenoalkoxy or halogenoalkylthio in each case having up to 4 carbon atoms, and where the hydrocarbon radical is optionally substituted up to 3 times by identical or different substituents from the group consisting of cycloalkyl having 3 to 8 carbon atoms, halogen, nitro, cyano, hydroxyl and —O—NO$_2$, or by aryl, aryloxy or arylthio in each case having 6 to 10 carbon atoms or by a 5- to 7-membered, saturated or unsaturated heretocycle having up to 3 heteroatoms from the group consisting of S, N and O, where the cycles for their part can be substituted up to 3 times by identical or different substituents from the group consisting of halogen and cyano or by straight-chain or branched alkyl, alkoxy, alkylthio, alkoxycarbonyl, halogenoalkyl, halogenoalkoxy or halogenoalkylthio in each case having up to 4 carbon atoms, or the hydrocarbon radical is substituted by a group of the formula —CO$_2$—R$^{14}$, —CONR$^{15}$R$^{16}$ or —NR$^{17}$R$^{18}$, in which $R^{14}$ has the abovementioned meaning of $R^{12}$ and is identical to or different from this and $R^{15}$, $R^{16}$, $R^{17}$ and $R^{18}$ have the abovementioned meaning of $R^7$ and $R^8$ and are identical to or different from these, $R^{10}$ and $R^{11}$ are identical or different and denote straight-chain or branched alkyl having up to 8 carbon atoms, or $R^{10}$ and $R^{11}$ together, including the oxygen atoms, form a 5- to 7-membered, saturated carbocycle, and their salts.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, ethanesulphonic acid, benzenesulphonic acid, toluenesulphonic acid or naphthalenedisulphonic acid.

The compounds according to the invention exist in stereoisomeric forms which behave either as image and mirror image (enantiomers), or which do not behave as image and mirror image (diastereomers). The invention relates both to the antipodes and to the racemic forms as well as to the diastereomer mixtures. Like the diastereomers, the racemic forms can be separated into the stereoisomerically homogeneous constituents in a known manner.

Preferred compounds of the general formula (I) are those in which $R^1$ represents straight-chain or branched alkyl having up to 6 carbon atoms, which is optionally substituted by hydroxyl, $R^2$ represents straight-chain or branched alkoxycarbonyl having up to 4 carbon atoms, which is optionally substituted by straight-chain or branched alkoxy having up to 3 carbon atoms, represents nitro, cyano or formyl, or $R^1$ and $R^2$ together form a ring of the formula

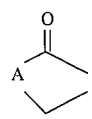

in which

A denotes an oxygen or sulphur atom, or the —CH$_2$— or —CH$_2$CH$_2$— group, $R^3$ represents a heterocyclic radical of the formula

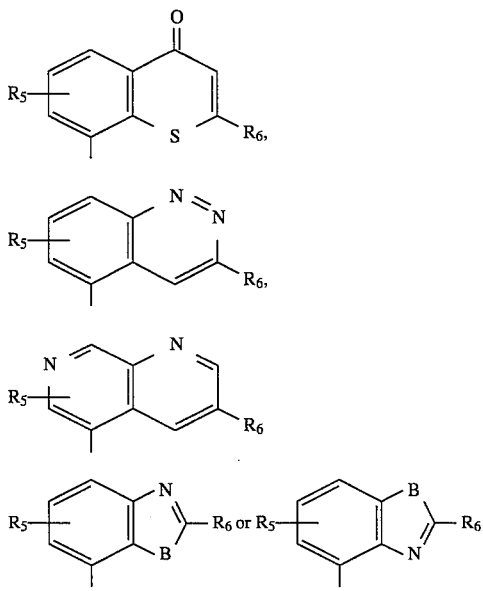

in which
B denotes an oxygen or sulphur atom,
$R^5$ denotes hydrogen, fluorine, chlorine or straight-chain or branched alkyl or alkoxy in each case having up to 2 carbon atoms,
$R^6$ denotes phenyl which is optionally substituted by fluorine, chlorine, nitro, cyano or trifluoromethyl or by straight-chain or branched alkyl or alkoxy in each case having up to 6 carbon atoms, or denotes straight-chain or branched alkyl having up to 10 carbon atoms, or denotes cyclopropyl, cyclohexyl or cyclopentyl, or denotes pyridyl or thienyl, which is optionally substituted by fluorine, chlorine or bromine,
$R^4$ represents a group of the formula $—CO—NR^7R^8$, $—CO—D—R^9$ or $—P(O)(OR^{10})(OR^{11})$, in which
$R^7$ and $R^8$ are identical or different and denote hydrogen or a straight-chain or branched, cyclic, saturated or unsaturated hydrocarbon radical having up to 6 carbon atoms, which is optionally substituted by cyclopropyl, cyclopentyl, cyclohexyl, fluorine, chlorine, bromine or hydroxyl or by phenyl or pyridyl, where the cycles for their part can be substituted by fluorine, chlorine or cyano or by straight-chain or branched alkyl, alkoxy, alkylthio, alkoxycarbonyl in each case having up to 3 carbon atoms, trifluoromethyl or trifluoromethoxy, or denote phenyl or pyridyl, which are optionally substituted by fluorine or chlorine or by straight-chain or branched alkyl, alkoxy, alkylthio, alkoxycarbonyl in each case having up to 4 carbon atoms, trifluoromethyl or trifluoromethoxy, or $R^7$ and $R^8$ together, including the nitrogen atom, form a 5- to 7-membered, saturated or unsaturated heterocycle which can optionally be interrupted by an oxygen atom or by a radical of the formula $S(O)_a$, $—CO—$ or $—NR^{12}$, in which
a denotes a number 0, 1 or 2,
$R^{12}$ denotes hydrogen or phenyl, or denotes a cyclic, straight-chain or branched, saturated or unsaturated hydrocarbon radical having up to 6 carbon atoms, which is optionally substituted by fluorine or chlorine, or by phenyl or pyridyl which for their part can be substituted by fluorine, chlorine, methyl, ethyl, methoxy, ethoxy, trifluoromethyl or trifluoromethoxy,
and the heterocycle is optionally substituted by straight-chain or branched alkoxy or alkylthio in each case having up to 3 carbon atoms, fluorine, chlorine, phenyl or pyridyl or by branched alkyl having up to 4 carbon atoms or benzyl,
D denotes a direct bond or an oxygen atom,
$R^9$ denotes hydrogen, phenyl, or pyridyl, which are optionally substituted by fluorine or chlorine or by straight-chain or branched alkyl, alkoxy or alkylthio in each case having up to 3 carbon atoms, trifluoromethyl or trifluoromethoxy, or denotes a cyclic, straight-chain or branched, saturated or unsaturated hydrocarbon radical having up to 10 carbon atoms, which is optionally interrupted up to 2 times by identical or different oxygen or $—CO—$, $—O—CO—$, $—NH—CO—$, $—SO_2—NH—$, $—NH—SO_2—$, $—S(O)_b—$ or $—NR^{13}$, in which
b has the abovementioned meaning of a and is identical to or different from this,
$R^{13}$ has the abovementioned meaning of $R^{12}$ and is identical to or different from this,
or the hydrocarbon radical is optionally interrupted up to 2 times by identical or different phenylidene or a cyclic radical of the formula

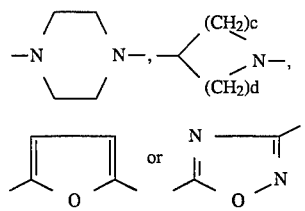

in which
c and d are identical or different and denote a number 1 or 2,
and where the hydrocarbon radical is optionally substituted up to 2 times by identical or different substituents from the group consisting of cyclopropyl, cyclopentyl, cyclohexyl, fluorine, chlorine, nitro, cyano, hydroxyl, $—O—NO_2$, straight-chain or branched alkylthio, alkoxy and acyloxy in each case having up to 6 carbon atoms or by phenyl, phenoxy, phenylthio or pyridyl, where the cycles for their part are substituted up to 2 times by identical or different substituents from the group consisting of fluorine, chlorine and cyano or by straight-chain or branched alkyl, alkoxy, alkylthio, alkoxycarbonyl in each case having up to 4 carbon atoms, trifluoromethyl or trifluoromethoxy, or the hydrocarbon radical is substituted by a group of the formula $—CO_2—R^{14}$, $—CONR^{15}R^{16}$ or $—NR^{17}R^{18}$, in which
$R^{14}$ has the abovementioned meaning of $R^{12}$ and is identical to or different from this and
$R^{15}$, $R^{16}$, $R^{17}$ and $R^{18}$ have the abovementioned meaning of $R^7$ and $R^8$ and are identical to or different from these,
$R^{10}$ and $R^{11}$ are identical or different and denote straight-chain or branched alkyl having up to 6 carbon atoms or
$R^{10}$ and $R^{11}$, including the oxygen atom, form a 6-membered saturated carbocycle,
and their salts.
Particularly preferred compounds of the general formula (I) are those
in which
$R^1$ represents straight-chain or branched alkyl having up to 4 carbon atoms, which is optionally substituted by hydroxyl, $R^2$ represents straight-chain or branched alkoxycarbonyl having up to 3 carbon atoms or methoxyethoxycarbonyl, or represents nitro, cyano or formyl, or $R^1$ and $R^2$ together form a lactone ring of the formula

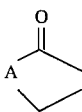

in which

A denotes an oxygen or sulphur atom or the —$CH_2$— or —$CH_2CH_2$— group, $R^3$ represents a heterocyclic radical of the formula

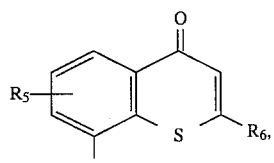

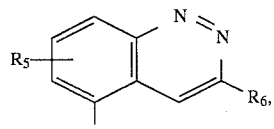

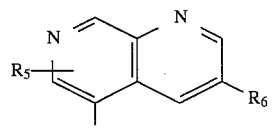

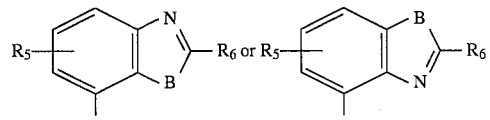

in which

B denotes an oxygen or sulphur atom, $R^5$ denotes hydrogen, chlorine or methyl, $R^6$ denotes phenyl which is optionally substituted by fluorine, chlorine, nitro or trifluoromethyl or by straight-chain or branched alkyl or alkoxy in each case having up to 4 carbon atoms, or denotes straight-chain or branched alkyl having up to 8 carbon atoms, or denotes cyclopropyl, cyclohexyl or cyclopentyl, or denotes pyridyl or thienyl, which is optionally substituted by fluorine, chlorine or bromine, $R^4$ represents a group of the formula —CO—$NR^7R^8$ or —CO—D—$R^9$, in which $R^7$ and $R^8$ are identical or different and denote hydrogen or phenyl or a straight-chain, branched, cyclic, saturated or unsaturated hydrocarbon radical having up to 6 carbon atoms, which is optionally substituted by phenyl which for its part can be substituted by fluorine, chlorine, methyl, ethyl, methoxy or ethoxy, D denotes a direct bond or an oxygen atom, $R^9$ denotes hydrogen or phenyl, or denotes a cyclic, straight-chain or branched, saturated or unsaturated hydrocarbon radical having up to 8 carbon atoms, which is optionally interrupted by oxygen or sulphur or by a radical of the formula —O—CO—, —NH—CO— or —$NR^{13}$, in which $R^{13}$ denotes hydrogen or straight-chain or branched alkyl having up to 4 carbon atoms, which is optionally substituted by phenyl, or denotes phenyl, and where the hydrocarbon radical is optionally substituted by cyclopropyl, cyclopentyl, cyclohexyl, fluorine, chlorine, cyano, hydroxyl, phenyl, phenoxy, phenylthio or pyridyl, or is substituted by a group of the formula —$CO_2$—$R^{14}$, —$CONR^{15}R^{16}$ or —$NR^{17}R^{18}$, in which $R^{14}$ has the abovementioned meaning of $R^{13}$ and is identical to or different from this and $R^{15}$, $R^{16}$, $R^{17}$ and $R^{18}$ have the abovementioned meaning of $R^7$ and $R^8$ and are identical to or different from these, and their salts.

The preparation of the compounds of the general formula (I) according to the invention is characterized in that

[A] either aldehydes Of the formula (II)

$$R^{13}—CHO \qquad (II)$$

in which $R^3$ has the abovementioned meaning, are reacted directly with compounds of the general formula (III)

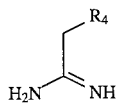    (III)

in which $R^1$ and $R^2$ have the abovementioned meaning, and compounds of the tautomeric formulae (IV) and (IVa)

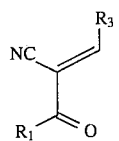    (IV)

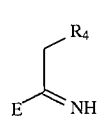    (IVa)

in which $R^4$ has the abovementioned meaning, in inert solvents at temperatures between 10° C. and 150° C., or

[B] ylidene compounds of the general formula (V)

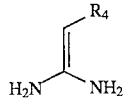    (V)

in which $R^1$ and $R^3$ have the abovementioned meaning, are reacted with compounds of the general formula (VI) or (VIA)

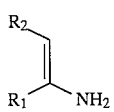    (VI)

-continued

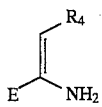

(VIa)

in which

R⁴ has the abovementioned meaning, and

E represents the amino group or $C_1$–$C_4$-alkoxy, if appropriate in the presence of inert organic solvents at temperatures from 10° C. to 150° C., where in the case in which E represents $C_1$–$C_4$-alkoxy, ammonium salts, such as ammonium acetate, are added.

In the case of the pure enantiomers, either the resulting diastereomer mixture of the respective compounds of the general formula (I) in which $R^2$ represents a defined chiral radical is first separated, then converted into the corresponding carboxylic acids and in a last step esterified or the respective diastereomers are transesterified directly using the appropriate alcohols, in particular in the form of the alkoxides.

The processes according to the invention can be illustrated, by way of example, by the following reaction scheme:

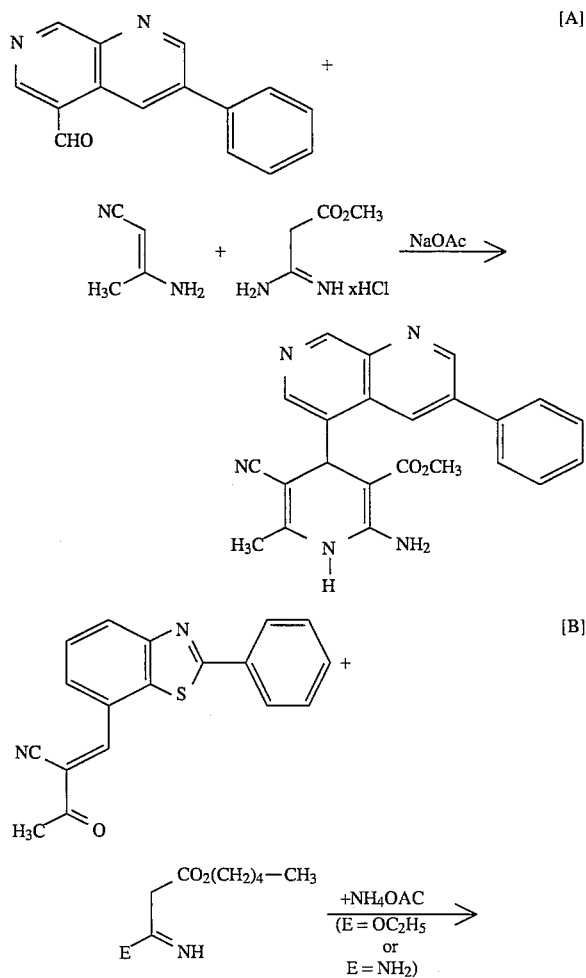

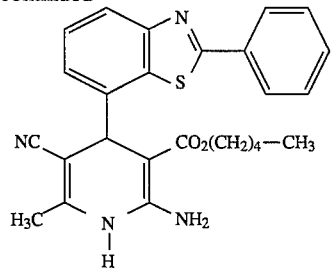

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride or hydrocarbons such as benzene or toluene. It is also possible to use mixtures of the solvents mentioned. Depending on the particular process variant [A] or [B], methanol, isopropanol, ethanol and n-propanol, acetonitrile or tetrahydrofuran are preferred.

The reaction temperatures can be varied within a substantial range. In general, the reaction is carried out between +10° C. and +150° C., preferably between +20° C. and +100° C., in particular at the boiling point of the respective solvent.

The reaction can be carried out at normal pressure, but also at elevated or reduced pressure (e.g. 0.5 to 3 bar). In general, it is carried out at normal pressure.

Suitable chiral ester radicals are all esters of enantiomerically pure alcohols such as, for example, 2-butanol, 1-phenylethanol, lactic acid, lactic acid esters, mandelic acid, mandelic acid esters, 2-aminoalcohols, sugar derivatives, hydroxyamino acid derivatives and many other enantiomerically pure alcohols.

The diastereomers are in general separated either by a fractional crystallization, by column chromatography or by Craig partition. Which is the optimum process must be decided from case to case, sometimes it is also expedient to use combinations of the individual processes. Separation by crystallization or Craig partition or a combination of both processes is particularly suitable.

The aldehydes of the general formula (II) are new in the case in which $R^3$ represents the radicals of the formula

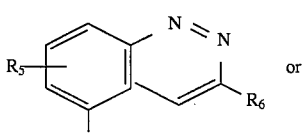

or

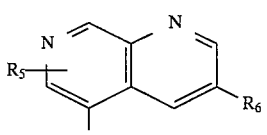

and can be prepared, for example, by a) reacting substituted pyridines of the general formula (VII)

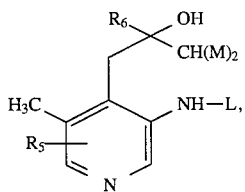

in which
R$^5$ has the abovementioned meaning and preferably represents chlorine,
R$^4$ has the abovementioned meaning,
L represents an amino protective group such as, for example, tert-butylcarbonyl and
M represents straight-chain or branched alkoxy having up to 4 carbon atoms,
first with protonic acids, preferably hydrochloric acid, and cyclizing with subsequent hydrogenation to give the compounds of the general formula (VIII)

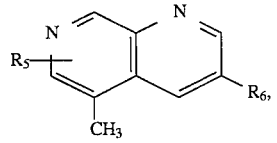

in which
R$^5$ and R$^6$ have the abovementioned meaning, and in a last step oxidizing the methyl group, preferably using selenium dioxide, in an organic solvent or naphthalene, preferably naphthalene, and in the case in which R$^3$ represents the radical of the formula

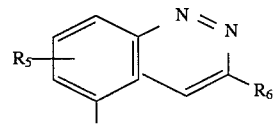

b) cyclizing compounds of the general formula (IX)

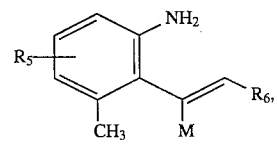

in which
R$^5$, R$^6$ and M have the abovementioned meaning,
via the diazotized stage (NH$_2$→N$_2^+$) to give compounds of the general formula (X)

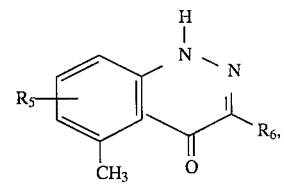

in which
R$^5$ and R$^6$ have the abovementioned meaning,
converting in a second step using PCl$_5$/POCl$_3$ into compounds of the general formula (XI)

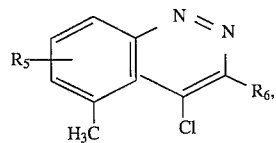

in which
R$^5$ and R$^6$ have the abovementioned meaning, hydrogenating and finally oxidizing the methyl group in inert solvents.

The aldehydes of the general formula (II), in which R$^3$ represents the radicals of the formula

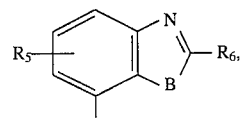

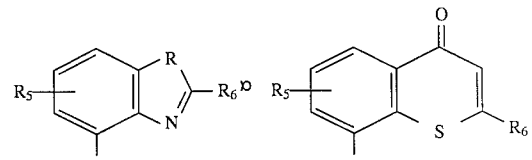

are known or can be prepared by customary methods.

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or amides such as hexamethylphosphoramide or dimethylformamide, or acetic acid and also methylene chloride, carbon tetrachloride or toluene. It is also possible to use mixtures of the solvents mentioned.

The compounds of the general formulae (VIII) and (X) are in general oxidized using oxidizing agents such as, for example, chromyl chloride, cerammonium nitrate, silver(II) oxide, selenium dioxide or a chromium(VI) oxide in combination with acetic anhydride. Selenium dioxide is preferred.

The oxidations can be carried out at normal pressure or elevated or reduced pressure (for example from 0.5 to 5 bar), preferably at normal pressure.

The compounds of the general formulae (VIII), (X) and (XI) are new and can be prepared by the abovementioned process.

The compounds of the general formula (VII) are new and can be prepared by reducing the 5-nitro group in the known compound 2-chloro-3,4-dimethyl-5-nitropyridine first to the corresponding 5-amino group by customary methods, for example by hydrogenation with H$_2$/Pd/C in dioxane, then blocking the amino group by reaction with pivaloyl chloride, intermediately deprotonating with n-butyllithium in tetrahydrofuran and in a last step reacting with 2,2-dialkoxyacetophenones.

The compounds of the general formulae (III), (IV), (IVa), (V), (VI), (VIa) and (IX) are known per se or can be prepared by customary methods.

The above preparation processes are only given for clarification. The preparation of the compounds of the formula (I) is not restricted to these processes, but any modification of these processes can be used in the same manner for the preparation of the compounds according to the invention.

The compounds according to the invention show an unforeseeable, useful spectrum of pharmacological action. They affect the contractility of the heart and the tone of the smooth musculature.

They can therefore be employed in medicaments for affecting pathologically modified blood pressure, as coronary therapeutics and for the treatment of cardiac insufficiency. They can moreover be used for the treatment of cardiac arrhythmias, for lowering the blood sugar, for the detumescence of mucous membranes and for affecting the salt and liquid balance.

The cardiac and vascular effects were found in the isolated perfused guinea-pig heart. To this end, the hearts of guinea pigs of 250 to 350 g in weight are used. The animals are killed by a blow to the head, the thorax is opened, and a metal cannula is tied into the exposed aorta. The heart is separated from the thorax with the lungs and attached via an aortic cannula to the perfusion apparatus with continuous perfusion. The lungs are separated at the lung roots. The perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), whose $CaCl_2$ content is 1.2 mmol/l. 10 mmol/l of glucose are added as an energy-producing substrate. Before perfusion, the solution is filtered free of particles. The solution is aerated with 95% $O_2$, 5% $CO_2$ to maintain the pH 7.4. The hearts are perfused under constant flow (10 ml/min) at 32° C. by means of a peristaltic pump.

To measure the cardiac function, a liquid-filled latex balloon which is connected to a pressure transducer via a liquid column is introduced into the left ventricle through the left auricle, and the isovolumetric contractions are recorded on a rapid recorder. The perfusion pressure is recorded by means of a pressure transducer which is connected to the perfusion system upstream of the heart. Under these conditions, a reduction in the perfusion pressure indicates a coronary dilation, an increase or decrease in the left-ventricular contraction amplitude a reduction or an increase in cardiac contractility. The compounds according to the invention are perfused, in suitable dilutions, into the perfusion system shortly upstream of the isolated heart.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate, using emulsifiers and/or dispersants, where e.g. in the case of the use of water as a diluent organic solvents can optionally be used as auxiliary solvents.

Administration is carried out in the customary manner, preferably orally or parenterally, in particular perlingually or intravenously.

In general, it has proven advantageous in the case of intravenous administration to administer amounts of about 0.001 to 1 mg/kg, preferably about 0.01 to 0.5 mg/kg of body weight to achieve effective results, and in the case of oral administration the dose is about 0.01 to 20 mg/kg, preferably 0.1 to 10 mg/kg of body weight.

In spite of this, it may sometimes be necessary to depart from the amounts mentioned, in particular depending on the body weight or the type of administration route, on individual behaviour towards the medicament, the manner of its formulation and the time or interval at which administration takes place. Thus, in some cases it may be sufficient to manage with less than the abovementioned minimum amount, while in other cases the abovementioned upper limit must be exceeded. In the case of the administration of relatively large amounts, it may be advisable to divide these into several individual doses over the course of the day.

EXAMPLE 1

Ethyl 2-amino-5-cyano-6-methyl-4-(3-phenyl-1,7-naphthyridin-5-yl)-1,4-dihydropyridine-3-carboxylate

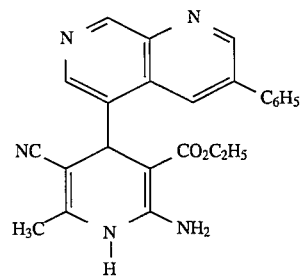

2 g (8.5 mmol) of 3-phenyl-1,7-naphthyridine-5-carboxaldehyde are suspended in 20 ml of ethanol and stirred with 0.7 ml (8.5 mmol) of 5-methylisoxazole. A solution of 196 mg of sodium in 14 ml of ethanol is added and the mixture is stirred for 2 hours at 50° C. 1.42 g of ethyl amidinoacetate hydrochloride and 0.51 ml (8.5 mmol) of acetic acid are added and the mixture is boiled for 16 hours. After cooling, 10 g of silica gel are added and the mixture is concentrated in vacuo. The residue is chromatographed on a silica gel column using toluene/ethyl acetate mixtures. After concentration of the pure fractions, the product is crystallized by trituration with ether. 2 g of crystals are obtained.

EXAMPLE 2

Isopropyl 2-amino-5-cyano-6-methyl-4-(3-(fluorophenyl)-1,7-naphthyridin-5-yl)-1,4-dihydropyridine-3-carboxylate

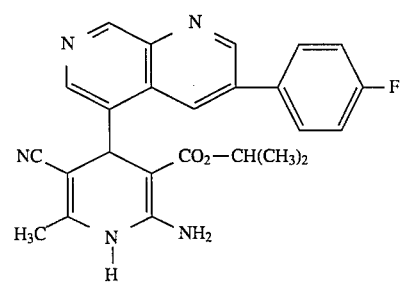

0.5 g (1.98 mmol) of 3-(4-fluorophenyl)-1,7-naphthyridine- 5-carboxaldehyde are dissolved in 20 ml of isopropanol and stirred with 0.161 ml of 5-methylisoxazole. A solution of 46 mg of sodium in 5 ml of isopropanol is added and the mixture is stirred for 2 hours at 50° C. 358 mg (1.98 mmol) of isopropyl amidinoacetate hydrochloride and 0.113 ml of glacial acetic acid are added and the mixture is boiled for 15 h. After cooling, 3 g of silica gel are added and the mixture is concentrated in vacuo. The residue is chromatographed on a silica gel column using toluene/ethyl acetate mixtures. After concentration of the pure fractions, the product is crystallized by trituration with ether. 104 mg of crystals are obtained.

The compounds shown in Tables 1 and 2 are prepared in analogy to the procedures of Examples 1 and 2:

TABLE 1

| Ex. No. | $R^3$ | $R^4$ | M.p. °C. |
|---|---|---|---|
| 3 | 2-phenyl-benzothiazol-7-yl | $-CO_2-C_2H_5$ | 232 |
| 4 | 2-phenyl-benzothiazol-7-yl | $-CO_2-CH(CH_3)_2$ | 233 |
| 5 | 3-phenyl-1,7-naphthyridin-5-yl | $-CO_2(CH_2)_2CH_3$ | 239 |
| 6 | 3-phenyl-1,7-naphthyridin-5-yl | $-CO_2CH(CH_3)_2$ | 250 |
| 7 | 3-(2-fluorophenyl)-1,7-naphthyridin-5-yl | $-CO_2CH(CH_3)_2$ | 226 |
| 8 | 3-phenyl-1,7-naphthyridin-5-yl | $-CO_2C_2H_5$ | 265 |

TABLE 2

[Structure: 1,4-dihydropyridine with aryl substituent bearing a thiochromone (phenyl-substituted) group, R1, R2, R4 substituents and NH2]

| Ex. No. | R¹ | R² | R⁴ | M.p. °C. | Enantiomer/Diastereomer/Rotation | |
|---|---|---|---|---|---|---|
| 9 | | ![acetyl-O] (−C(=O)−CH with O) | −CO₂−C₂H₅ | | | |
| 10 | −CH₂−OH | −CO₂−C₂H₅ | −CO₂C₂H₅ | | | |
| 11 | −CH₃ | −CN | −CO₂−C₂H₅ | | | |
| 12 | −CH₃ | −CN | −CO₂−CH(CH₃)₂ | | | |
| 13 | −CH₃ | −CN | −CO₂C₂H₅ | 243 (Decomp.) | (+) $[\alpha]_D = +224.44$ (c = 0.59/CHCl₃) | |
| 14 | −CH₃ | −CN | −CO₂−CH(CH₃)₂ | 243 (Decomp.) | (+) $[\alpha]_D = +225.52$ (c = 0.535/CHCl₃) | |
| 15 | −CH₃ | −CN | −CO₂CH(CH₃)₂ | 256 (Decomp.) | $[\alpha]_D = -219.45$ (c = 0.851/CHCl₃) | |
| 16 | −CH₃ | −CN | −CO₂−C(CH₃)(H)−CO₂CH₃ | | | Diastereomers |
| 17 | −CH₃ | −CN | −CO₂−C(CH₃)(H)−CO₂CH₃ | | (+) $[\alpha]_D = 229.75$ (c = 0.7735/CHCl₃)  $[\alpha]_D = -137.78$ (c = 0.8465/CHCl₃) | |
| 18 | −CH₃ | −CN | −CO₂−C₂H₅ | 257 (Decomp.) | (−) $[\alpha]_D = -220.73$ (c = 0.7113/CHCl₃) | |
| 19 | −CH₃ | −CN | −CO₂CH₃ | Foam | (−) $[\alpha]_D = -231.64$ (c = 0.8205/CHCl₃) | |
| 20 | −CH₃ | −CN | −CO₂−(CH₂)₂−OH | Foam | (−) $[\alpha]_D = -208.87$ (c = 0.8455/CHCl₃) | |
| 21 | −CH₃ | −CN | −CO₂−(CH₂)₂−OCH₃ | Foam | (−) $[\alpha]_D = -204.27$ (c = 0.716/CHCl₃) | |
| 22 | | ![acetyl-S] (−C(=O)−CH with S) | −CO₂−CH(CH₃)₂ | | | |

We claim:

1. An aldehyde of the formula

R³—CHO   (II)

in which

R³ represents a radical of the formula

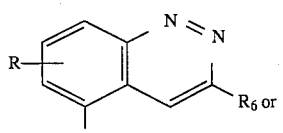

-continued
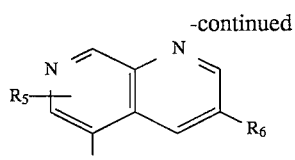
in which
R⁵ denotes hydrogen, halogen or straight-chain or branched alkyl or alkoxy in each case having up to 8 carbon atoms, and
R⁶ denotes straight-chain or branched alkyl having up to 12 carbon atoms, or denotes cycloalkyl having 3 to 8 carbon atom.
* * * * *

UNITED STATES PATENT AND TRADEMARK OFFICE
CERTIFICATE OF CORRECTION

PATENT NO. : 5,478,937

DATED : December 26, 1995

INVENTOR(S) : Straub, et al.

It is certified that error appears in the above-identified patent and that said Letters Patent is hereby corrected as shown below:

Col. 18, line 60    Delete " 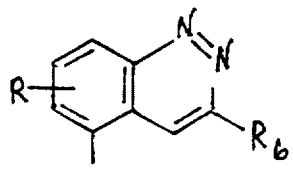 " and substitute

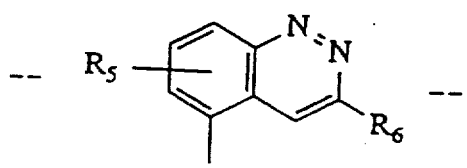

Signed and Sealed this

Eleventh Day of June, 1996

Attest:

BRUCE LEHMAN

*Attesting Officer*        *Commissioner of Patents and Trademarks*